United States Patent
Balla

(10) Patent No.: US 9,084,515 B1
(45) Date of Patent: Jul. 21, 2015

(54) DIABETIC TOE WASH

(71) Applicant: Albert Balla, Corbin, KY (US)

(72) Inventor: Albert Balla, Corbin, KY (US)

(73) Assignee: Albert Balla, Corbin, KY (US)

( * ) Notice: Subject to any disclaimer, the term of this patent is extended or adjusted under 35 U.S.C. 154(b) by 399 days.

(21) Appl. No.: 13/317,235

(22) Filed: Dec. 27, 2012

(51) Int. Cl.
*A61M 35/00* (2006.01)
*A47K 7/04* (2006.01)
*A61M 37/00* (2006.01)
*A47C 4/00* (2006.01)
*A47C 1/12* (2006.01)

(52) U.S. Cl.
CPC .............. *A47K 7/04* (2013.01); *A61M 35/00* (2013.01); *A61M 37/00* (2013.01)

(58) Field of Classification Search
CPC ........ A61M 35/00; A61M 37/00; A47C 4/00; A47C 1/12; A47C 1/00; B60N 2/02
See application file for complete search history.

(56) References Cited

U.S. PATENT DOCUMENTS

| | | | | |
|---|---|---|---|---|
| 4,383,488 | A * | 5/1983 | Macho et al. | 108/129 |
| 5,876,091 | A * | 3/1999 | Chernomashentsev | 297/16.2 |
| 7,485,111 | B1 * | 2/2009 | Choi et al. | 604/289 |
| 7,938,811 | B2 * | 5/2011 | Furukawa | 604/293 |

* cited by examiner

*Primary Examiner* — Tatyana Zalukaeva
*Assistant Examiner* — Ilya Treyger

(57) ABSTRACT

The Ten Toe Rejuvenator (TTR) is a 24.4 inch long ABS injection molded plastic with a front and rear bracket. A one inch wide band of fleece material is wrapped around the two brackets in a figure eight fashion. This design is to allow the user to hold one end of the TTR, place the fleece around a toe and wash and dry it completely or to apply medication. User may stand or sit while using the TTR.

1 Claim, 1 Drawing Sheet

① BODY
② FLEECE BAND 1 INCH WIDE
③ FRONT BRACKET
④ REAR BRACKET

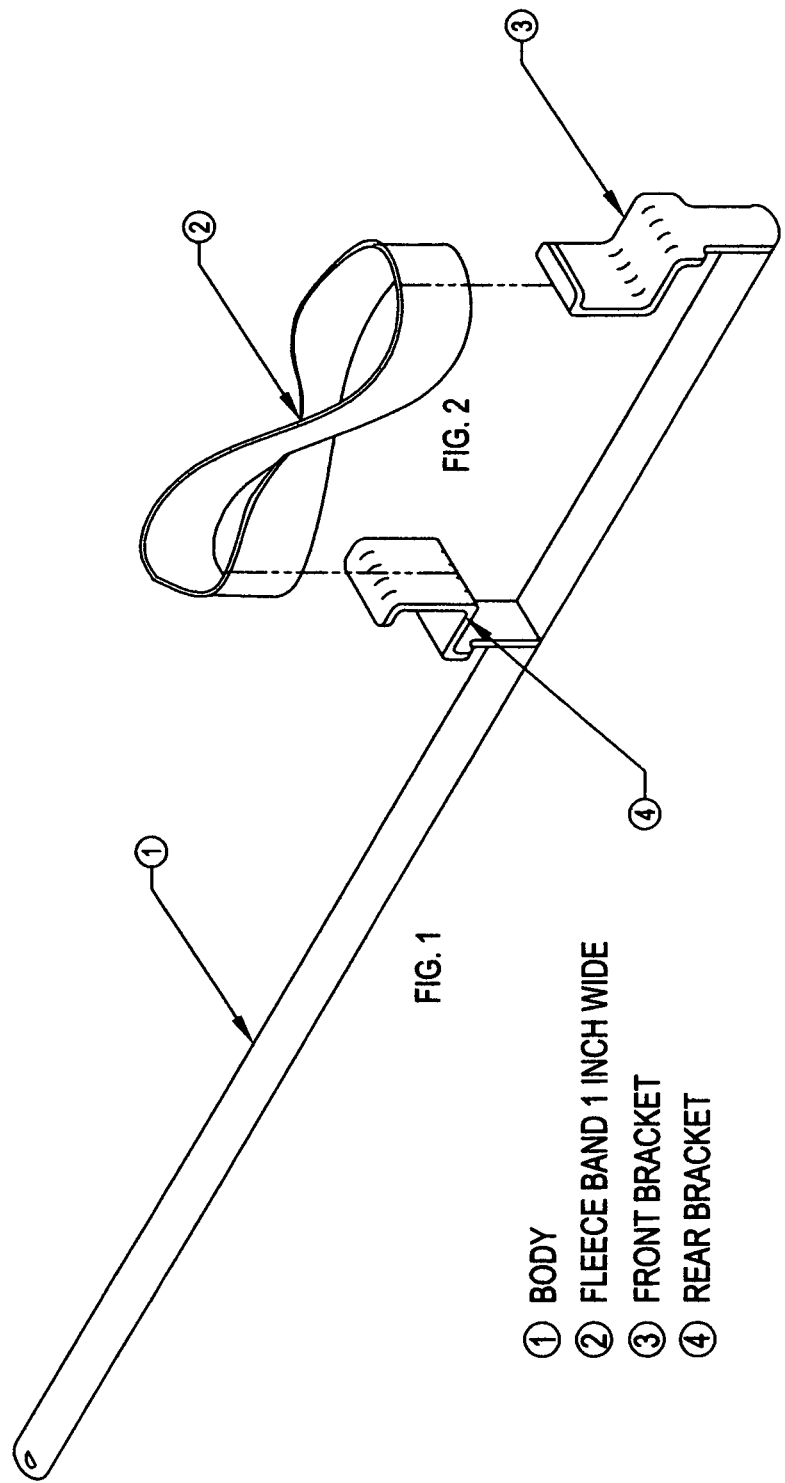

DIABETIC TOE WASH

A commonly posed problem with diabetic patients is how to thoroughly clean and dry between toes, a vital part of diabetic foot health. This invention, ten toes rejuvenator, (1) diabetic toe wash allows diabetic patients to wash and dry between their toes without having to bend in uncomfortable and sometimes impossible positions. At the present time no other product is available on the market to assist in with this procedure. The extra long handle (FIG. 1) allows patients to sit comfortably and take care of their feet the same time. Ten toes rejuvenator will be equipped with a soft fleece band, (FIG. 2) allowing for gentle cleansing and drying between the toes. In addition to cleansing, medications such as lotions, creams, ointments, etc. can easily be applied to the toes with a reusable fleece band. (FIG. 2)

Overall size: 24" length×0.75" width
Construction: abs injection molded plastic

FIG. 1 depicts the handle which on end has a front and rear Brackets which FIG. 2 is attached.

FIG. 2 depicts the 1 inch wide fleece band which soap or Medication is applied and rubbed between the toes.

The ten toe Rejuvenator (TTR) for applying a medication to a diabetic toe that measures 24.4 inches, the TTR comprising a base that measures 24.4 inches in length, wherein a distal end of the base is adapted to be held by a patient when in use, a pair of injection molding plastic brackets spaced from each other at the distance sufficient to accommodate the diabetic foot, and a one inch wide fleece band wrapped around the brackets in figure eight fashion configured to be wrapped around the diabetic toe in order to wash, dry and apply the medication to said diabetic toe.

The invention claimed is:

1. The Ten Toe Rejuvenator (TTR) for applying a medication to a diabetic toe, the TTR comprising a base that measures 24.4 inches in length, wherein a distal end of the base is adapted to be held by a patient when in use, a pair of injection molding plastic brackets spaced from each other at the distance sufficient to accommodate the diabetic foot, and a one inch wide fleece band wrapped around the brackets in figure eight fashion configured to be wrapped around the diabetic toe in order to wash, dry and apply the medication to said diabetic toe.

* * * * *